(12) United States Patent
Bouchard et al.

(10) Patent No.: US 9,993,621 B2
(45) Date of Patent: Jun. 12, 2018

(54) ADAPTABLE SLEEVE FOR CATHETER SECUREMENT AND PROTECTION

(71) Applicants: Briana M. Bouchard, Madbury, NH (US); Diana A. Burns, Madbury, NH (US); Logan J. Driscoll, Madbury, NH (US); Claire K. Rogers, Madbury, NH (US)

(72) Inventors: Briana M. Bouchard, Madbury, NH (US); Diana A. Burns, Madbury, NH (US); Logan J. Driscoll, Madbury, NH (US); Claire K. Rogers, Madbury, NH (US)

( * ) Notice: Subject to any disclaimer, the term of this patent is extended or adjusted under 35 U.S.C. 154(b) by 524 days.

(21) Appl. No.: 14/680,619

(22) Filed: Apr. 7, 2015

(65) Prior Publication Data

US 2015/0283358 A1 Oct. 8, 2015

Related U.S. Application Data

(60) Provisional application No. 61/975,996, filed on Apr. 7, 2014.

(51) Int. Cl.
*A61M 25/00* (2006.01)
*A61M 25/02* (2006.01)

(52) U.S. Cl.
CPC ..... *A61M 25/02* (2013.01); *A61M 2025/0206* (2013.01); *A61M 2025/0213* (2013.01); *A61M 2025/0246* (2013.01)

(58) Field of Classification Search
CPC .... A61M 2025/0213; A61M 2025/026; A61M 25/02; A61M 2025/0246; A61M 2025/0206; A61M 2025/028; A61M 2025/0253; A61F 5/4408
See application file for complete search history.

(56) References Cited

U.S. PATENT DOCUMENTS

| | | | | |
|---|---|---|---|---|
| 2,266,230 A * | 12/1941 | Mazzeo | ................... | A61M 5/52 128/877 |
| 3,794,032 A * | 2/1974 | Derouineau | .......... | A61M 25/02 604/248 |
| 4,008,532 A * | 2/1977 | Kilbourn | .............. | A43B 5/0415 36/118.9 |
| 4,397,647 A * | 8/1983 | Gordon | .................. | A61M 25/02 128/DIG. 26 |
| 4,470,410 A * | 9/1984 | Elliott | ..................... | A61M 5/52 128/877 |
| 4,666,434 A * | 5/1987 | Kaufman | .............. | A61M 25/02 128/DIG. 26 |
| 4,671,787 A * | 6/1987 | Widman | ............... | A61M 25/02 128/DIG. 15 |
| 4,799,923 A * | 1/1989 | Campbell | ............. | A61M 25/02 128/DIG. 26 |

(Continued)

OTHER PUBLICATIONS http://www.redpointcorp.com/stedline-features, Feb. 24, 2015.

*Primary Examiner* — Scott Medway

(57) ABSTRACT

An adaptable sleeve for securing a catheter in place and protecting it once secured is provided. The sleeve provides a body configured to wrap about a catheter insertion location, a cover to protect the catheter once inserted, and a hub attachment mechanism to hold the catheter hub and prevent its movement relative to the insertion site, once inserted.

17 Claims, 6 Drawing Sheets

(56) References Cited

U.S. PATENT DOCUMENTS

| | | | | |
|---|---|---|---|---|
| 4,846,807 A * | 7/1989 | Safadago | A61M 5/158 | |
| | | | 128/DIG. 26 | |
| 4,870,976 A * | 10/1989 | Denny | A61M 25/02 | |
| | | | 128/877 | |
| 4,941,479 A * | 7/1990 | Russell | A61F 5/05858 | |
| | | | 128/854 | |
| 5,048,512 A * | 9/1991 | Turner | A61J 15/0015 | |
| | | | 128/876 | |
| 5,131,412 A * | 7/1992 | Rankin | A61F 5/3761 | |
| | | | 128/869 | |
| 5,263,497 A * | 11/1993 | Grabenkort | A61B 5/0084 | |
| | | | 128/869 | |
| 5,403,285 A * | 4/1995 | Roberts | A61M 25/02 | |
| | | | 604/179 | |
| 5,426,872 A * | 6/1995 | Hayes | A43B 5/04 | |
| | | | 36/117.1 | |
| 5,496,282 A * | 3/1996 | Militzer | A61M 25/02 | |
| | | | 128/DIG. 26 | |
| 5,549,567 A * | 8/1996 | Wolman | A61M 25/02 | |
| | | | 128/DIG. 26 | |
| 5,897,519 A * | 4/1999 | Shesol | A61M 25/02 | |
| | | | 602/75 | |
| 6,258,066 B1 * | 7/2001 | Urich | A61M 25/02 | |
| | | | 604/174 | |
| 6,544,232 B1 * | 4/2003 | McDaniel | A61M 25/02 | |
| | | | 128/DIG. 26 | |
| 6,892,733 B2 * | 5/2005 | Clinton | A61F 5/0109 | |
| | | | 128/878 | |
| 7,182,088 B2 * | 2/2007 | Jenkins | A61M 5/52 | |
| | | | 128/878 | |
| 7,284,729 B2 * | 10/2007 | Walsh | A61M 25/02 | |
| | | | 128/877 | |
| 8,109,912 B2 * | 2/2012 | Alferness | A61M 5/14248 | |
| | | | 604/181 | |
| 8,197,447 B2 * | 6/2012 | Wright | A61M 5/158 | |
| | | | 128/846 | |
| 8,277,419 B1 | 10/2012 | Spitaleri | | |
| 9,205,021 B2 * | 12/2015 | Malhi | A61H 23/04 | |
| 9,387,306 B2 * | 7/2016 | Andreae | A61M 25/02 | |
| 2002/0128605 A1 * | 9/2002 | Miller | A61M 25/02 | |
| | | | 604/172 | |
| 2007/0049871 A1 * | 3/2007 | Fleischer | A61M 25/02 | |
| | | | 604/180 | |
| 2007/0135719 A1 * | 6/2007 | Booth | A61B 5/02233 | |
| | | | 600/490 | |
| 2007/0156111 A1 * | 7/2007 | Dalal | A61F 13/15203 | |
| | | | 604/389 | |
| 2013/0012883 A1 * | 1/2013 | Fitzgerald | A61M 25/02 | |
| | | | 604/179 | |
| 2016/0106958 A1 * | 4/2016 | Price | A61L 29/00 | |
| | | | 604/179 | |

* cited by examiner

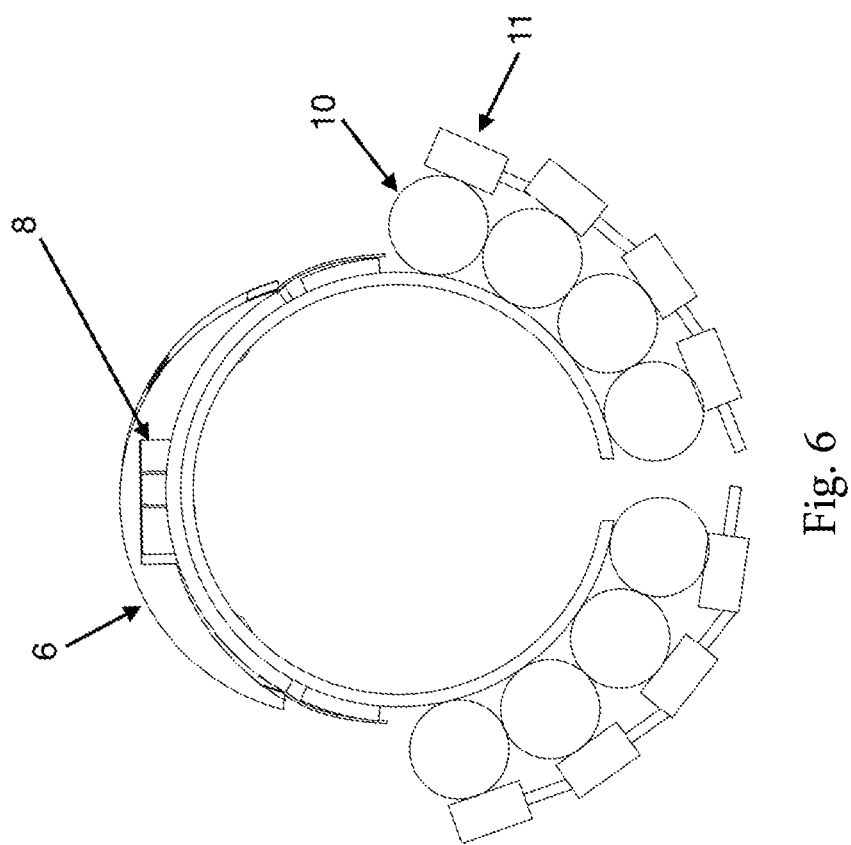

ADAPTABLE SLEEVE FOR CATHETER SECUREMENT AND PROTECTION

FIELD OF THE INVENTION

The present invention relates generally to catheter securement and site protection devices. More particularly, the present invention relates to a fabric sleeve that wraps around, or otherwise secures to, a patient's arm (or other body part or body surface), providing both joint immobilization and as catheter-site protection and catheter securement.

DESCRIPTION OF RELATED ART

Most emergency medical patients and serious or chronic illness patients will receive a catheter of some sort during the course of their treatment. This could be as simple as a catheter saline drip or a central line (etc.). However, these catheters can result in patient infection, discomfort, and irritation (both mental and physical). These complications are especially prevalent in the pediatric and geriatric populations, where patients may not always understand why the catheter is attached or what it's doing. This misunderstanding can result in patient-initiated line removal, infiltration and infection. Furthermore, nurses and doctors do not have an effective catheter method to prevent these complications. In order to do so, stabilization, securement, visibility, comfort and protection are needed. Additionally, the area must be clean and free of any interfering components.

Therefore, what is needed is a device that may safely and effectively provide for catheter site protection and securement.

SUMMARY OF THE INVENTION

The subject matter of this application may involve, in some cases, interrelated products, alternative solutions to a particular problem, and/or a plurality of different uses of a single system or article.

In one aspect, an adaptable sleeve for catheter securement is provided. The device includes a sleeve formed of a flexible material and adapted to be wrapped about a body part of a user. The sleeve further defines a central aperture through which a catheter inserted into the patient may pass. A removable cover is attached to the sleeve, covering the aperture when in a closed position, and exposing the aperture of the sleeve when in an open position. A hub attachment device is removably attached to the sleeve. The hub attachment device comprises a protrusion sized to receive a hub of the catheter for holding it in place. The hub attachment device further comprises at least one securement strip extending away from the protrusion, the at least one securement strip being removably connected to the sleeve.

In another aspect, an adaptable sleeve for catheter securement is provided. The device includes a sleeve formed of a plurality of strips, each of the plurality of strips connected to an adjacent of the plurality of strips along a length of the strips. The sleeve as structured is adapted to be wrapped about a body part of a user. The sleeve further defines a central aperture through which a catheter inserted into the patient may pass. A removable cover is attached to the sleeve, covering the aperture when in a closed position, and exposing the aperture of the sleeve when in an open position. A hub attachment device is removably attached to the sleeve. The hub attachment device comprises a protrusion sized to receive a hub of the catheter for holding it in place. The hub attachment device further comprises at least one securement strip extending away from the protrusion, the at least one securement strip being removably connected to the sleeve.

BRIEF DESCRIPTION OF THE DRAWINGS

FIG. 6 provides a front cutaway view of still another embodiment of the present invention.

DETAILED DESCRIPTION

Figure 1:
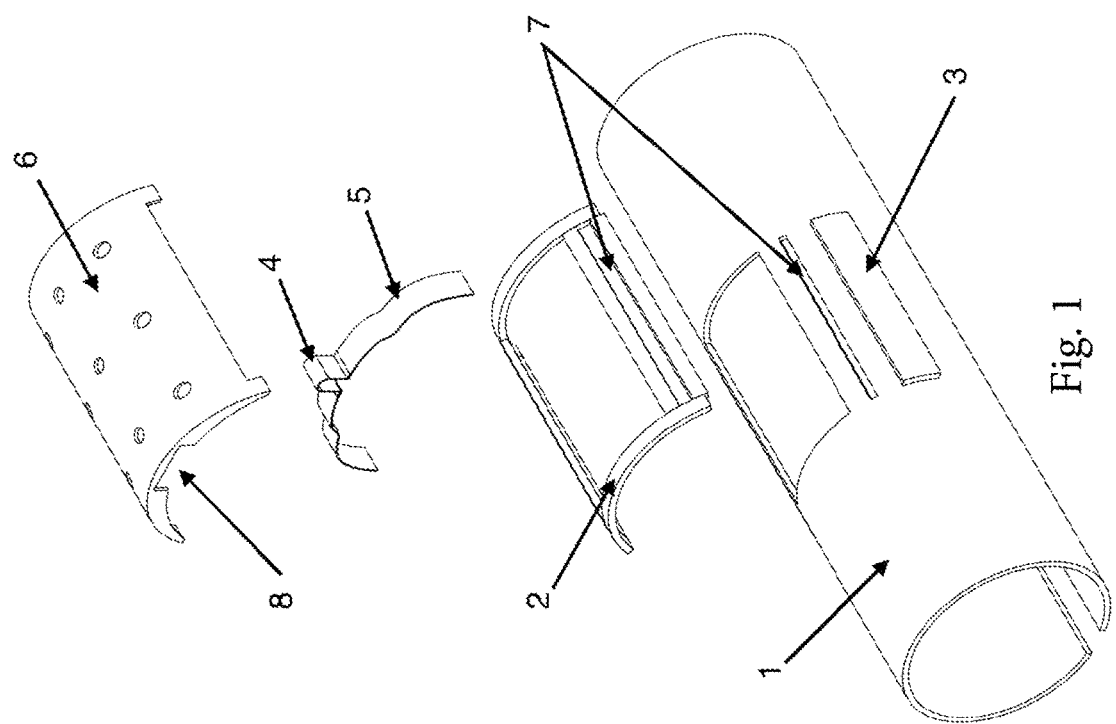
FIG. 1 provides an exploded view of an embodiment of the present invention.

The detailed description set forth below in connection with the appended drawings is intended as a description of presently preferred embodiments of the invention and does not represent the only forms in which the present invention may be constructed and/or utilized. The description sets forth the functions and the sequence of steps for constructing and operating the invention in connection with the illustrated embodiments.

Generally, the present invention concerns a fabric sleeve that wraps around a patient's arm, allowing in-joint immobilization, catheter-site protection and/or catheter securement. The sleeve may have a puncture site opening that provides easy access to the catheter insertion site or other skin puncture sites. Additionally, this device incorporates catheter stabilization, protects the catheter site from being disturbed, and eliminates the need for tape in securing the catheter line. Overall, this sleeve solves the many problems caused by traditional catheter securement, while causing minimal interference with standard catheter insertion procedures.

In one embodiment, the present invention is a device that incorporates catheter securement and arm (or other joint or area) stabilization while eliminating the need for tape. It is designed to work with existing medical supplies and does not require any significant alterations to catheter insertion protocol. The overall result is that a flexible, cylindrical sleeve can slide or wrap onto a patient's arm until a catheter site opening exposes the desired region for catheter insertion.

The sleeve of the present invention is the primary and largest piece of the device. The sleeve may be made of a flexible fabric or skin compatible material, though its manufacture is not limited to such materials. The sleeve may open lengthwise and be lined with a securement on one side of the sleeve, which allows it to be wrapped around the patient's arm, elbow, wrist, chest hand or other body part (depending on embodiment) to the desired tightness after the catheter is inserted. The nature of the material should allow the device to be comfortably but securely held in place. It should be understood that in other embodiments, a securement other than wrapping may be used without straying from the scope of this invention.

A hub attachment mechanism connects to a hub of the catheter line and maintains the placement and alignment of the catheter. The sleeve design allows for the placement of the hub attachment mechanism anywhere within the access region. Hub attachment mechanism can be removably, adjustably, or permanently attachable to the sleeve. For example, it may be attached to the sleeve by securement strips that are optionally fed through a cover and placed along the sides of the sleeve.

Due to the possible deformation of the sleeve material, a support structure or structures may be needed along the sides of the access region of the sleeve and/or the sleeve itself to maintain the sleeve and access region's shape. The support structure embodiments that run the length of the arm could be made of rigid material and could be sewn onto the fabric in one embodiment. Supports may also run circumferentially, in another embodiment, and could be made of flexible material. Such supports could also be attached by sewing. In a particular embodiment, the supports may also provide easy attachment of a catheter cover.

A clear, plastic cover may be placed and/or positioned over the catheter insertion site. The cover is connected at the top of the access region, and will clip in at the bottom. Serving as a very important security measure, this prevents the patient from being able to directly access the catheter lines.

In one embodiment, removable supports may be attached to the outer circumference of the sleeve. These supports are removable members that run the all or part of the length of the device and prevent the patient from bending his or her arm. In one embodiment, the outer circumference of the device may have pockets where the motion restriction supports can be inserted (or removed) to provide joint immobilization.

Another embodiment of the present invention may address re-distributing the pressure applied to the skin by having multiple application points which would reduce the force per area. This embodiment will form a sleeve to secure the arm by surrounding the arm with rods such as hollow rods of a suitable material. In one embodiment, these rods may be filled with a gas, foam, or similar material. The rods would be separated by a small space to allow airflow and equally distribute the pressure at the interface between the rod and the skin.

In this embodiment, top rods on either side of the arm may be attached by additional rods stretching across the arm or a strap that locks the device together.

For stability and rigidity, the outer (non-skin facing) surface area of each rod may be attached to a rigid bar that covers a full length or nearly full length of the rod. One particularly novel aspect of this invention is the attachment between the rigid outer rod and the next adjacent one in series. The goal being to attach the rods together with a locking clasp that would allow the nurse to add or remove as many rod components as necessary to wrap around the outside of the arm. This design has the crucial benefit of being a one size fits all, however the downside is the requirement of some sort of assembly for each device.

In another embodiment, a protective covering may be placed over the catheter site to prevent the patient from tampering with the catheter or any other critical or dangerous components. In one embodiment, the cover may be transparent or translucent. The cover preferably closes and is only openable with a particular action, making it at least slightly difficult to open, the open position allowing access to the catheter. For example, the cover may have a keyed or other secured lock in one embodiment. In another embodiment, the cover may have a sliding mechanism allowing it to open. In still another embodiment a certain action may be required such as a pushing down of the cover before it can be opened, similar to a "child lock" system.

This embodiment focuses on an ability to stabilize the arm/elbow. Pockets and stiffer structural materials are implemented to prevent any arm movement. Stabilizer pockets are designed so that the user may insert or remove rigid or partially rigid stabilizing rods based on each patient's particular need. This component allows for device flexibility if necessary and complete restriction when required.

In operation, application of the present device requires four simple steps:

Insert a catheter—As the first step in catheter administration, a nurse inserts the catheter into the patient, and a piece of Tegaderm is placed directly over the catheter site. This is the only piece of adhesive needed with this device, as it is preferable to provide a barrier for bacteria.

Attach the Sleeve—The sleeve of the present invention is then wrapped around the patient's arm, and secured with the built-in hook and loop fastener, buttons, or other securement mechanism.

Secure catheter Line—The catheter may now be connected to the hub attachment mechanism. The nurse will secure the catheter into the hub attachment mechanism, and attach it, through slits on either side of the cover of the present invention, to the sleeve.

Close Cover—The final step includes attaching the catheter line to the catheter and securing the protective plastic covering over the entire access area.

While varying embodiments have been discussed with respect to an arm applied embodiment, it should be understood that the present invention may be used around a wrist, forearm, shoulder, legs, torso, and any other area of the body where a catheter may be desired to be inserted.

Figure 2:
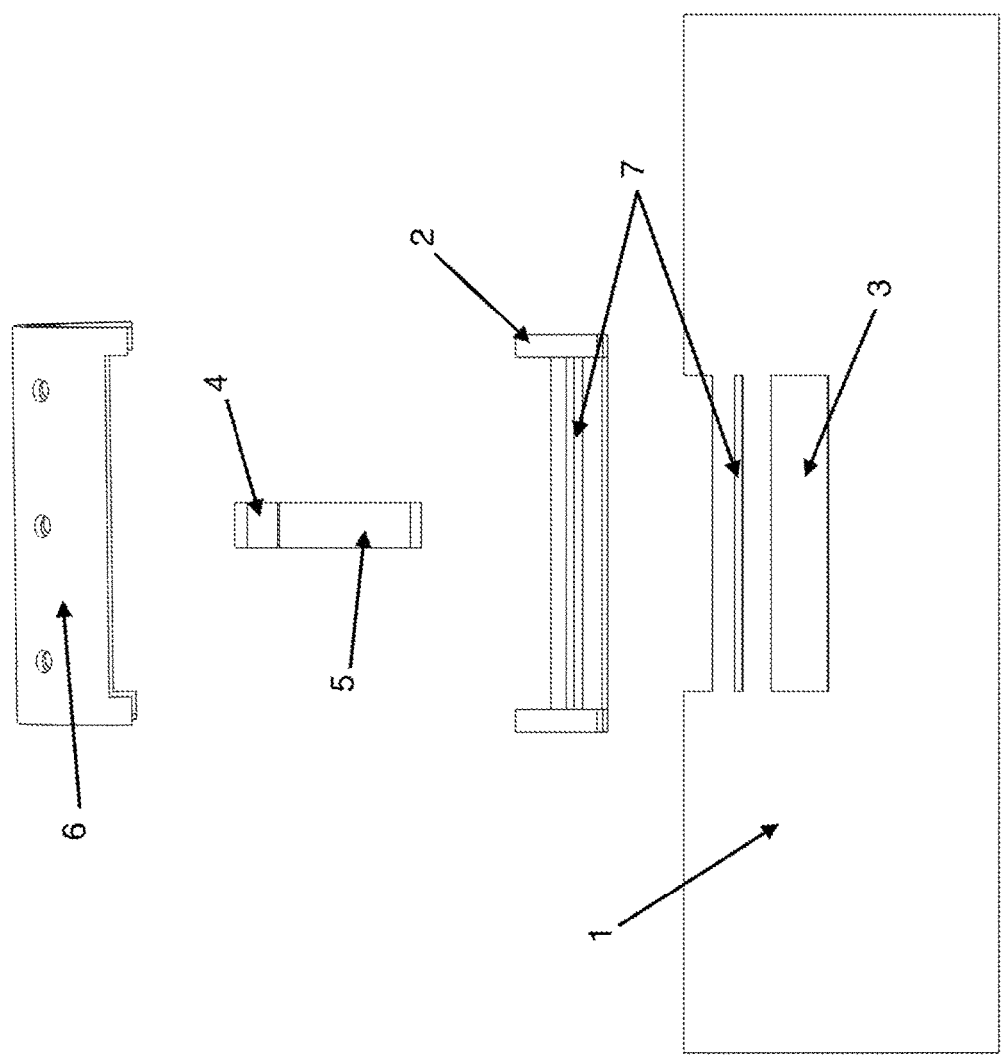
FIG. 2 provides an exploded view of an embodiment of the present invention.

Turning now to FIGS. 1 and 2, an exploded perspective and side view of an embodiment of the present invention is provided. In this view, sleeve 1 provides the base for the device. The sleeve 1 may be any material capable of wrapping around a body part, such as fabric, mesh, or the like. Sleeve defines a large central aperture exposing a skin of a wearer. In this central aperture is where the catheter may be inserted. A support structure 2 bounds the central aperture of the sleeve 1. The support structure 2 is configured to maintain the shape of the aperture and hold the sleeve 1 in place relative to the skin exposed by the aperture. Hook and loop connectors 3 are positioned on opposite sides of the sleeve 1, across the aperture. In other embodiments, these connectors 3 may be any structure allowing connection thereto. A hub attachment mechanism 4 is used to attach to the sleeve 1 and hold the catheter in place. The mechanism 4 includes a protrusion at its center configured to receive the catheter hub. Securement strips 5 are on opposite sides of the protrusion and attach to the hook and loop connectors 3 on either side of the aperture. In this embodiment, these securement strips 5 may pass through slots 7 in both the support structure 2 and sleeve 1. A cover 6 is configured to attach over a top of the aperture. This may be by connection to the support structure 2 or another part of the sleeve. The cover 6 defines a line slot 8 so that a catheter line such as tubing may connect to the catheter when the cover is closed.

Figure 3:
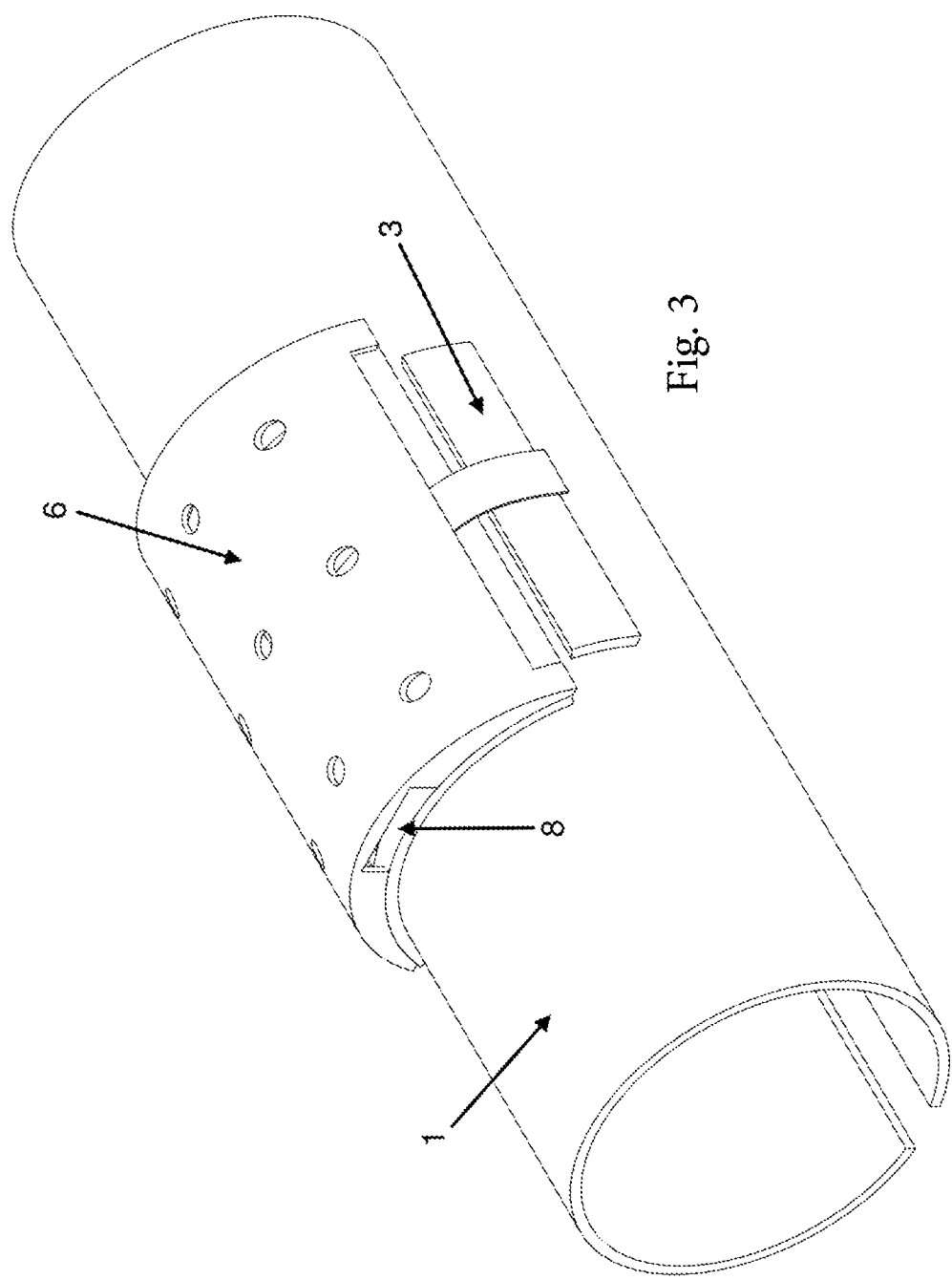
FIG. 3 provides a perspective view of another embodiment of the present invention.

FIG. 3 shows another embodiment of the present invention with the cover in a closed position. In this view, the sleeve, 1 has the cover 6 attached to it, via support structure (not shown). The line slot 8 can be seen to provide access to the sleeve 1 aperture by a small item such as a catheter line. The securement strip 5 of the hub attachment mechanism is attached to hook and loop connector 3, holding it in place. In this embodiment, sleeve 1 is not completely closed, instead having an opening along its bottom length. This opening allow for adaptability in attaching the device to varying sized arms or other body parts. A connecting structure (not shown) may allow the sleeve 1 to connect to the body part or, in other embodiments, the sleeve 1 may be flexibly held in shape, and may deform over various sized arm and stay in place.

Figure 4:
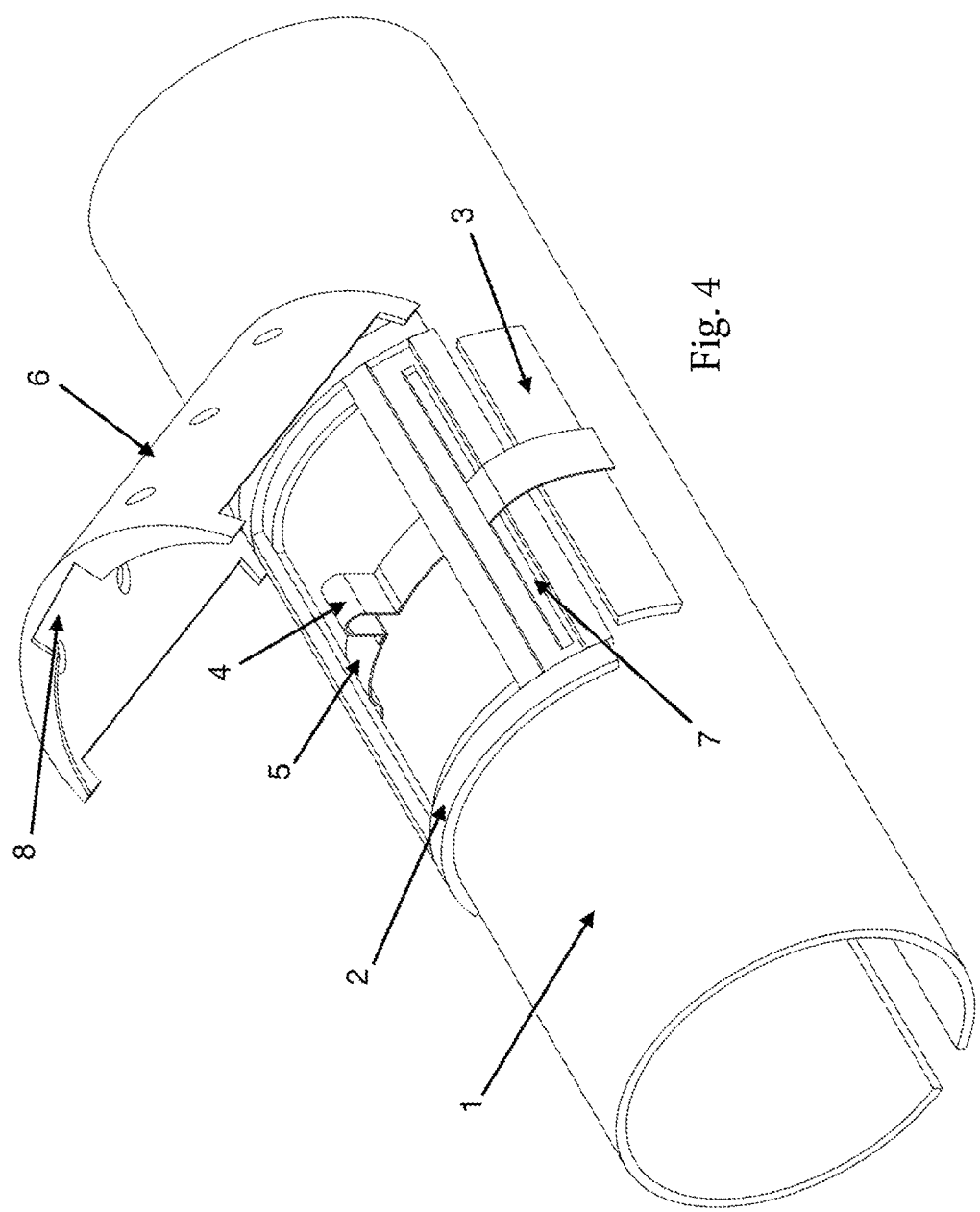
FIG. 4 provides a perspective view of yet another embodiment of the present invention.

FIG. 4 provides a perspective view of another embodiment of the present invention having a cover in an open position. In this embodiment, the cover 6 is hingedly attached at a widthwise end to the support structure 2. However, in varying embodiments, the cover 6 may attach in a number of different ways, such as a lengthwise hinge, fully removable connection, and the like. In this embodiment, the hub attachment mechanism 4 is shown attached and in position. Securement strip 5 is attached to the hook and loop connector 3 to hold the hub attachment mechanism 4 in place. The strip 5 passes through slot 7 of the sleeve 1 and support structure 2.

Figure 5:
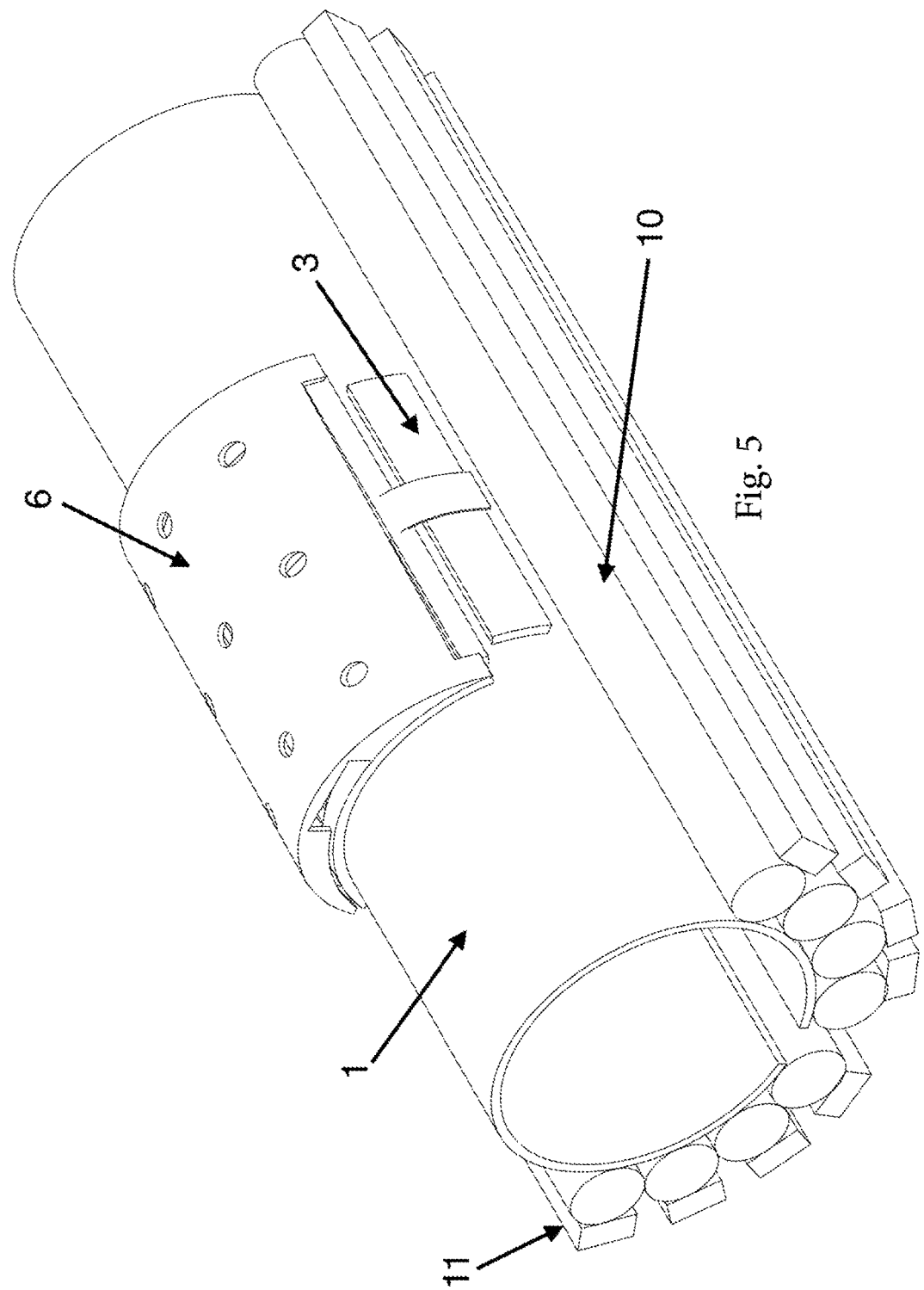
FIG. 5 provides a perspective view of another embodiment of the present invention.

FIGS. 5 and 6 provides a perspective and front cross sectional view respectively of still another embodiment of the present invention. In this embodiment, instead of or in addition to the sleeve 1 of FIG. 1 for example, a rigid outer material 11 may define or at least partially define the body of the device. The rigid outer material 11 is formed of a plurality of strips attached together along their lengths. In one embodiment, each of the plurality of strips 11 is connected in serial to an adjacent strip 11 by a hinged removable connection, allowing the strips 11, once connected, to pivot with respect to each other. In a particular embodiment, a first side of a rigid strip 11 may have a female removable hinged connector, while a second side may have a male removable hinged connector, such that a first side of a first strip 11 may be attached to a second side of a second strip, allowing a plurality of strips to be formed together, and allowing the device to be modular depending on size of the body part to which the rigid outer material 11 is to be connected. In this embodiment, a plurality of air or foam rods 10 is positioned between the rigid outer material 11 and the body part to which the device is attached. The hub attachment mechanism 4 connects to a top one of the rigid outer material 11 strip on each side of the device, and in other embodiments may attach to the top air or foam rod 10. The cover (not shown but shown in FIGS. 1-4) may connect over the top of the hub attachment mechanism 4 when in a closed position. In the embodiment shown, sleeve 1 is also included, however it should be understood that in other embodiments, the sleeve may be formed by rods 10.

While several variations of the present invention have been illustrated by way of example in preferred or particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

What is claimed is:

1. An adaptable sleeve for catheter securement comprising:
   a sleeve, the sleeve formed of a flexible material and adapted to be secured to a body surface of a user, the sleeve defining a central aperture through which a catheter inserted into the user may pass;
   a cover attachable to the sleeve, the cover covering the aperture of the sleeve when in a closed position, and exposing the aperture of the sleeve when in an open position;
   a hub attachment device removably attached to the sleeve, the hub attachment device comprising a protrusion sized to receive a hub of the catheter, holding it in place, and further comprising at least one securement strip extending away from the protrusion, the at least one securement strip being removably connected to the sleeve, the securement strip passed through a slot defined in the sleeve.

2. The adaptable sleeve for catheter securement of claim 1 further comprising a support structure bounding the aperture of the sleeve.

3. The adaptable sleeve for catheter securement of claim 1 further comprising a reinforcement attached along a length of the sleeve.

4. The adaptable sleeve for catheter securement of claim 1 further comprising a reinforcement about a circumference of the sleeve.

5. The adaptable sleeve for catheter securement of claim 1 wherein the cover is attached to the sleeve by a widthwise hinge.

6. The adaptable sleeve for catheter securement of claim 1 wherein the cover is attached to the sleeve by a lengthwise hinge.

7. The adaptable sleeve for catheter securement of claim 1 wherein the cover is lockable in the closed position.

8. The adaptable sleeve for catheter securement of claim 1 wherein the sleeve further comprises a pocket along its length, the pocket sized to receive a reinforcement strip.

9. The adaptable sleeve for catheter securement of claim 1 wherein the sleeve is adapted to wrap about a forearm of a user.

10. An adaptable sleeve for catheter securement comprising:
    a sleeve, the sleeve formed of a plurality of strips, each of the plurality of strips connected to an adjacent of the plurality of strips along a length of the strips; the sleeve adapted to be secured to body surface of a user, the sleeve defining a central aperture through which a catheter inserted into the user may pass;
    a cover attachable to the sleeve, the cover covering the aperture of the sleeve when in a closed position, and exposing the aperture of the sleeve when in an open position;
    a hub attachment device removably attached to the sleeve, the hub attachment device comprising a protrusion sized to receive a hub of the catheter, holding it in place, and further comprising at least one securement strip extending away from the protrusion, the at least one securement strip being removably connected to the sleeve, the securement strip passed through a slot defined in the sleeve.

11. The adaptable sleeve for catheter securement of claim 10 further comprising a support structure bounding the aperture of the sleeve.

12. The adaptable sleeve for catheter securement of claim 10 further comprising a reinforcement attached along a length of the sleeve.

13. The adaptable sleeve for catheter securement of claim 10 further comprising a reinforcement about a circumference of the sleeve.

14. The adaptable sleeve for catheter securement of claim 10 wherein the cover is attached to the sleeve by a widthwise hinge.

15. The adaptable sleeve for catheter securement of claim 10 wherein the cover is attached to the sleeve by a lengthwise hinge.

16. The adaptable sleeve for catheter securement of claim 10 wherein the cover is lockable in the closed position.

17. The adaptable sleeve for catheter securement of claim 1 wherein the sleeve is adapted to wrap about a forearm of a user.

* * * * *